United States Patent [19]

Richardson

[11] Patent Number: 5,149,329
[45] Date of Patent: Sep. 22, 1992

[54] SURGICAL SUTURE CARRIER AND METHOD FOR URINARY BLADDER NECK SUSPENSION

[75] Inventor: David A. Richardson, Farmington Hills, Mich.

[73] Assignee: Wayne State University, Detroit, Mich.

[21] Appl. No.: 626,184

[22] Filed: Dec. 12, 1990

[51] Int. Cl.$^5$ .............................................. A61B 19/00
[52] U.S. Cl. .................................... 604/272; 606/119; 128/898; 600/29
[58] Field of Search .......................... 600/29, 30, 31; 604/272; 606/119, 145, 222, 44, 139, 223

[56] References Cited

U.S. PATENT DOCUMENTS

| | | | |
|---|---|---|---|
| 2,738,790 | 3/1956 | Todt et al. | 606/145 |
| 4,019,498 | 4/1977 | Hawtrey et al. | |
| 4,128,686 | 12/1978 | Kyle et al. | |
| 4,172,458 | 10/1979 | Pereyra | |
| 4,584,990 | 4/1986 | Haber et al. | |
| 4,686,962 | 8/1987 | Haber | |
| 4,709,690 | 12/1987 | Haber | |
| 4,727,887 | 3/1988 | Haber | |
| 4,773,393 | 9/1988 | Haber et al. | 600/30 |
| 4,786,276 | 11/1988 | Haber | |
| 4,800,900 | 1/1989 | French | 128/885 |
| 4,802,479 | 2/1989 | Haber et al. | |
| 4,832,680 | 5/1989 | Haber et al. | 600/31 |
| 4,892,520 | 1/1990 | Gilbaugh | 604/272 |
| 5,013,292 | 5/1991 | Lemay | 600/30 |

OTHER PUBLICATIONS

Robertson, R. Jackson, "Instruments and Methods", Obstericts and Gynecology, vol. 41, No. 4, Apr. 1973 pp. 624–627.
Stamey, Thomas A., "Endoscopic Suspension of the Vesical Neck for Urinary Incontinence", Surgery Gynecology and Obstetrics, vol. 136, pp. 547–554, Apr. 1973.

Primary Examiner—Stephen C. Pellegrino
Assistant Examiner—Gary Jackson
Attorney, Agent, or Firm—Brooks & Kushman

[57] ABSTRACT

A suturing needle assembly used in a surgical operation to correct anatomical stress urinary incontinence, the suturing needle assembly having a needle and a sheath. The needle has an elongated flexible portion and a rigid portion which defines a tip for piercing tissue and an eyelet for removably attaching surgical thread. The sheath may selectively envelop the needle when it is beneficial to protect the patient and surgeon from the sharp tip. The flexibility and length of the needle and the sheath allow the suturing needle assembly to navigate a contoured internal passageway such as a female reproductive tract. According to a method of the present invention, the suturing needle assembly, laden with surgical thread, is inserted into a patient's vagina and guided to an operating site at the superior wall of the vagina below the urinary bladder neck. At the operating site, the needle tip is thrust through the superior wall of the vagina and into the retropubic space a sufficient number of times so that the superior wall of the vagina may be elevated and bound to structures in the retropubic space. As a result, problems of stress urinary incontinence are alleviated using the suturing needle assembly in a procedure which avoids needle stick of the surgeon's fingers.

14 Claims, 2 Drawing Sheets

SURGICAL SUTURE CARRIER AND METHOD FOR URINARY BLADDER NECK SUSPENSION

TECHNICAL FIELD

The present invention relates to a suturing needle assembly whose length, flexibility and sheathing are adapted for vaginal access to a patient's retropubic space, thereby facilitating surgical suspension of a prolapsed urinary bladder neck.

BACKGROUND ART

Anatomical stress urinary incontinence is a condition characterized by the involuntary escape of urine through the urethra during coughing, sneezing, or other stress-producing actions. This escape does not normally occur because the urethra, in its natural position, is elevated and constricted by the fascia and muscles which suspend it from the pubic bone. Under normal conditions, this structure prevents involuntary escape of urine under conditions of increased intra-abdominal pressure.

In a patient with anatomical stress urinary incontinence, however, the urethra may have become prolapsed and unconstricted because the endopelvic fascia have been stretched or weakened. Childbirth, hysterectomy, menopause and weakened pelvic support can contribute to this weakening. With the urethra in a prolapsed condition, a sneeze or cough could cause enough pressure in the bladder to expel urine through the unconstricted urethra. Various therapies, surgical and non-surgical, have been devised to correct the condition.

The non-surgical therapies often center on the principle of introducing a substance into the urethral region which will cause a constriction. U.S. Pat. No. 4,019,498 issued to Hawtrey et al. discloses a mushroom-shaped plastic mass which, when inserted into the vagina, exerts an upward thrust against the superior wall of the vagina of sufficient magnitude to block the flow of urine through the urethra. One disadvantage of this therapy is the attendant discomfort caused by the presence of the mass in the vagina.

U.S. Pat. No. 4,686,962 issued to Haber discloses an eliptoidally-shaped containment membrane which may be hypodermically implanted between the urethra and the subcutaneous corpus spongiousum and inflated to increase tissue volume. The disadvantages of this device include the introduction of synthetic objects into the body, and possible discomfort due to the presence or shifting of the membrane.

Among the surgical therapies is a surgically implanted occlusion cup disclosed by Haber in U.S. Pat. No. 4,584,990. The cup surrounds, engages, and constricts the urethra. The disadvantages of this device are similar to those associated with the disclosures of U.S. Patent Nos. 4,019,498 and 4,686,962 as discussed above.

The traditional surgical method of correcting bladder neck prolapse is the so-called abdominal approach to retropubic surgery. In this procedure, a large incision is made in the abdomen and a suturing needle is inserted through this incision and into the vagina. The vaginal fascia is thereby sutured to supporting structures in the retropubic region. The procedure, however, has significantly high morbidity because of the presence of several large blood vessels in the operating region. It is not uncommon for the needles to slip or tear through these blood vessels and cause significant bleeding. Another disadvantage of the abdominal approach is the risk of punctures to the surgeon's finger as the finger, while inserted in the vagina, guides the suturing needle through the vaginal fascia. Such punctures could lead to transmission of hepatitis, auto-immune deficiency virus (AIDS) and other serious diseases.

U.S. Pat. No. 4,172,458 issued to Pereyra discloses a ligature carrier for use in a suspension-type of operation that is different than the abdominal approach. In the Modified Pereyra Procedure, the tissues of the elevated superior wall of the vagina on each side of the urethra are sutured to the fascia of the abdominal wall instead of the structures in the retropubic region. The Modified Pereyra Procedure involves a blind excursion of a needle proximal to the bladder. The needle is inserted through an abdominal incision into the retropubic space and from there punctures the superior wall of the vagina. Because the surgeon cannot see the tip while it is being inserted, he necessarily guides it with his fingertip. This practice leads to a high risk of incisions into the surgeon's fingers; as with the abdominal approach, hepatitis and auto-immune deficiency virus are among the more serious diseases transmittable through such incisions. There exists also the risk of puncturing the bladder during the blind excursion of the needle. In addition, sutures have been left in the bladder which can lead to incontinence from an unstable bladder and also to bladder stones. The Pereyra procedure, in addition to its various surgical risks, has an unsatisfactorily high failure rate. This results from the use of the abdominal wall fascia as supporting structures for the bladder neck. All too often, sutures placed into the fascia pull through the tissue thereby causing bladder neck descent and resulting incontinence.

Against this background, a need has been developed for a surgical device and procedure which offers decreased morbidity and greater efficacy than the modified Pereyra procedure. The procedure must offer an alternative to the blind excursion of a sharp needle in the bladder and reproductive tract region. Before the present invention, there has been no technique which offers this alternative to patients suffering from anatomical urinary stress incontinence.

DISCLOSURE OF INVENTION

The present invention provides a surgical tool and method for its use which overcomes the problems and limitations of the prior art.

The invention allows for permanent correction of bladder neck prolapse by binding together the superior wall of the vagina and the pelvic supporting structures in the retropubic space. The present technique, unlike the abdominal approach and the Pereyra procedure, permits vaginal access and provides for needle sheathing. This combination of features greatly reduces the risks of punctures to the bladder, blood vessels or the surgeon's finger. As a result, the technique has a lower morbidity rate as compared to the other techniques and a higher efficiency rate than the Pereyra procedure because the present technique uses the stronger structures available in the retropubic space.

Accordingly, it is a general object of this invention to provide a treatment for the problem of anatomical stress urinary incontinence which is efficient, and permanent, and has a low morbidity rate.

It is another object of this invention to provide a suturing needle assembly having the characteristics of flexibility, needle sheathing for protection and hygiene, and simplicity in suture threading.

It is still another object of this invention to provide a method for using the disclosed suturing needle assembly in an operation to correct the problem of anatomical stress urinary incontinence.

In carrying out the above objects, a suturing needle assembly and a method for its use in urinary bladder neck suspension are provided. The suturing needle assembly has an elongated needle and a sheath. The needle has a flexible portion and a rigid portion. The flexible portion allows the needle to gain access through a curved internal passageway to an operating site. The rigid portion has a sharp tip for piercing tissues and an eyelet for surgical thread and is adapted for accurate placement of the surgical thread. The sheath encapsulates the needle during excursion through the curved passageway to protect the patient and the surgeon who guides it from laceration. The needle and sheath may be held in engagement, and the entire suturing needle assembly encapsulated by a protective cover during shipment and disposal.

The method of the present invention comprises using the suturing needle assembly in a surgical operation to correct prolapse of the urinary bladder neck. According to the method, the suturing needle assembly is inserted into a patient's vagina and deployed in the vagina and the retropubic space to bind the elevated superior wall of the vagina to structures in the retropubic space, thereby elevating the bladder neck.

The above objects and other objects, features and advantages of the present invention are readily apparent from the following detailed description of the best mode for carrying out the invention when taken in connection with the accompanying drawings.

BRIEF DESCRIPTION OF THE DRAWINGS

FIG. 7 is a block diagram illustrating the steps of the method of the present invention.

BEST MODES FOR CARRYING OUT THE INVENTION

Figure 1:
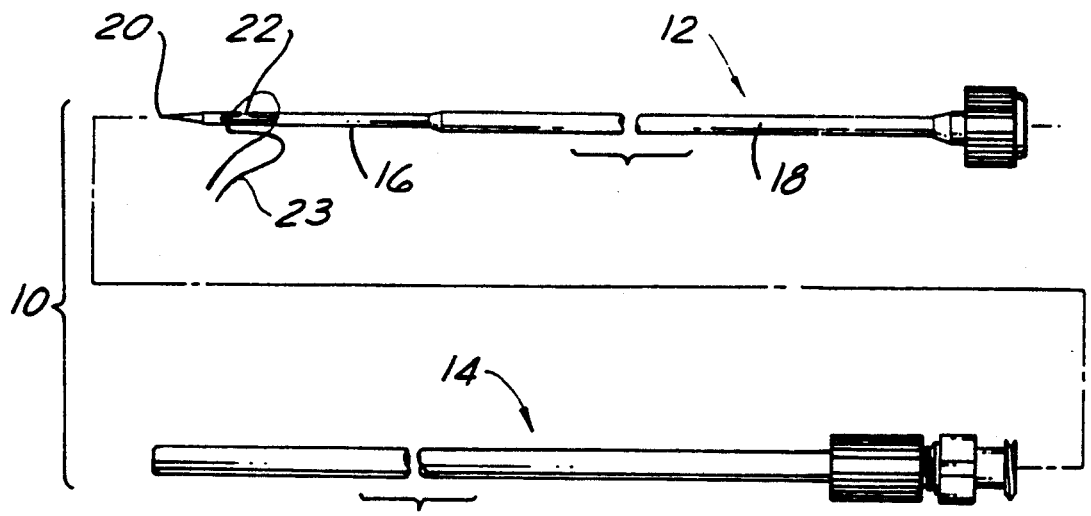
FIG. 1 is an exploded perspective view of a suturing needle assembly according to the present invention.

Turning first to FIG. 1, a suturing needle assembly of the present invention is illustrated with the reference numeral 10. The suturing needle assembly 10 includes an elongated flexible needle 12 and a flexible sheath 14. The needle 12 further includes a rigid portion 16 at its leading end and a flexible portion 18 at its trailing end.

The rigid portion 16 has a sharp tip 20 for piercing body tissue and an eyelet 22 for detachably attaching surgical thread 23. The eyelet 22 is T-shaped to facilitate ease in loading and unloading of surgical thread 23 and also to securely retain thread 23 as the rigid portion 16 is propelled into and withdrawn from tissue.

The flexible portion 18 may be selected from sections of various lengths and is preferably formed of extrudable thermoplastic with a low modulus of flexibility. The length of the flexible portion 18 will vary directly with the relative distance between an entrance site and an operating site. The low modulus of flexibility of the flexible portion 18 allows it to traverse a curved pathway between the entrance site and the operating site.

Figure 2:
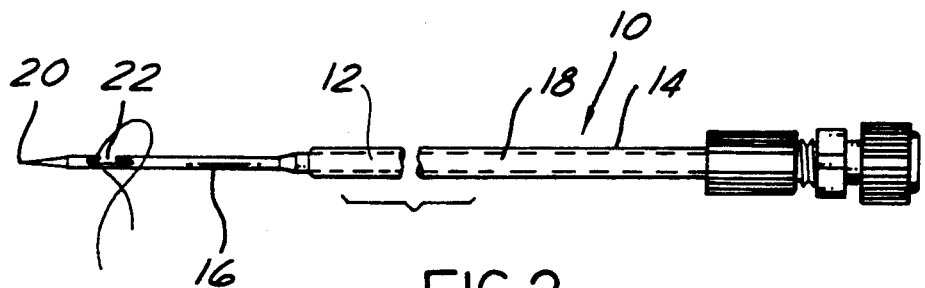
FIG. 2 is a side elevational view of the suturing needle assembly wherein a sheath is retracted from a needle to expose a rigid portion of the needle.
Figure 3:
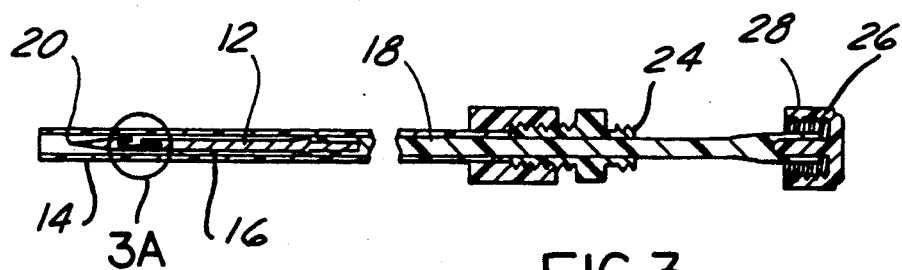
FIG. 3 is a side view in section of the suturing needle assembly having the sheath extended over the rigid portion of the needle.
Figure 3A:
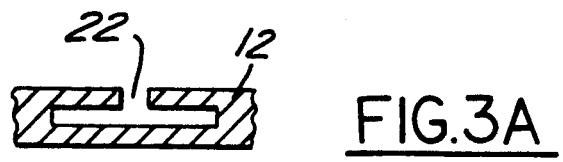
FIG. 3a is an enlarged view of the eye of FIGS. 1 and 3.

The sheath 14 is provided to envelop most of the needle 12. The sheath 14 is formed from a hollow tube whose inside diameter is slightly larger than the outside diameter of the flexible portion 18. The sheath is also formed of a low modulus, extrudable thermoplastic material. As shown in FIG. 2, the sheath 14 in its retracted position envelops the flexible portion 18 while leaving exposed the rigid portion 16 of the needle 12. Referring now to FIG. 3, the sheath 14 is shown extended past the needle tip 20, thereby completely enveloping the rigid portion 16 and leaving exposed a length of the flexible portion 18. Having the tip 20 covered by the sheath 14 in this way allows the suturing needle assembly 10 to traverse an internal passageway without risk of lacerations or punctures to patient or doctor.

FIG. 3 shows male screw threads 24 disposed on the sheath 14 and female screw threads 26 disposed on a knob 28 attached to the flexible portion 18. The screw threads 24 and 26 are helpful in that they allow the sheath 14 and needle 12 to be engaged when the suturing needle assembly 10 is not in use, thereby reducing the risk of injury from improper handling.

Figure 4:
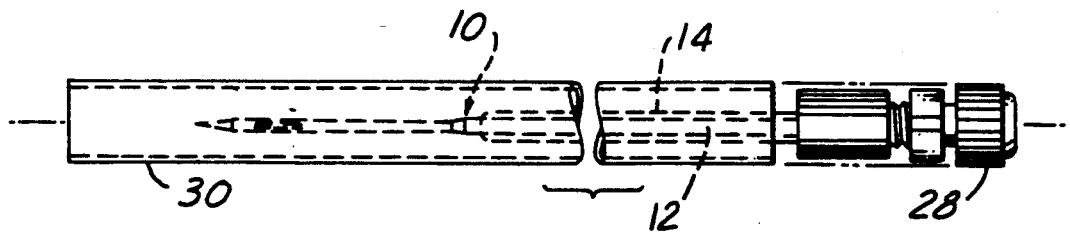
FIG. 4 is a side elevational view of the suturing needle assembly having a protective cover.

The threaded engagement is also helpful during transhipment and disposal. It is preferred that the needle tip 20 be encapsulated at all times preceding and following surgery. There is shown in FIG. 4 a cover 30 which may be used to encapsulate the suturing needle assembly 10. The cover 30 is a hollow cylinder with open ends and an inside diameter approximating the effective diameter of the knob 28. The suturing needle assembly 10 is most effectively protected when the sheath 14 and the needle 12 are engaged and encapsulated by the cover 30 which frictionally affixes to the knob 28.

Figure 5:
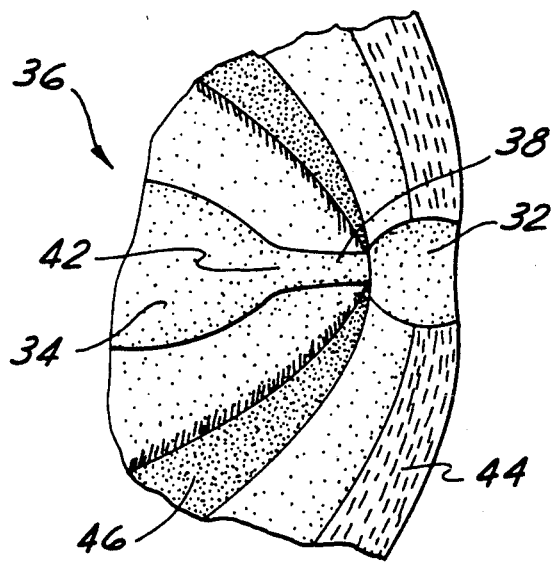
FIG. 5 is a plan view of the retropubic space showing the supporting structures and location of surgical sutures.
Figure 6:
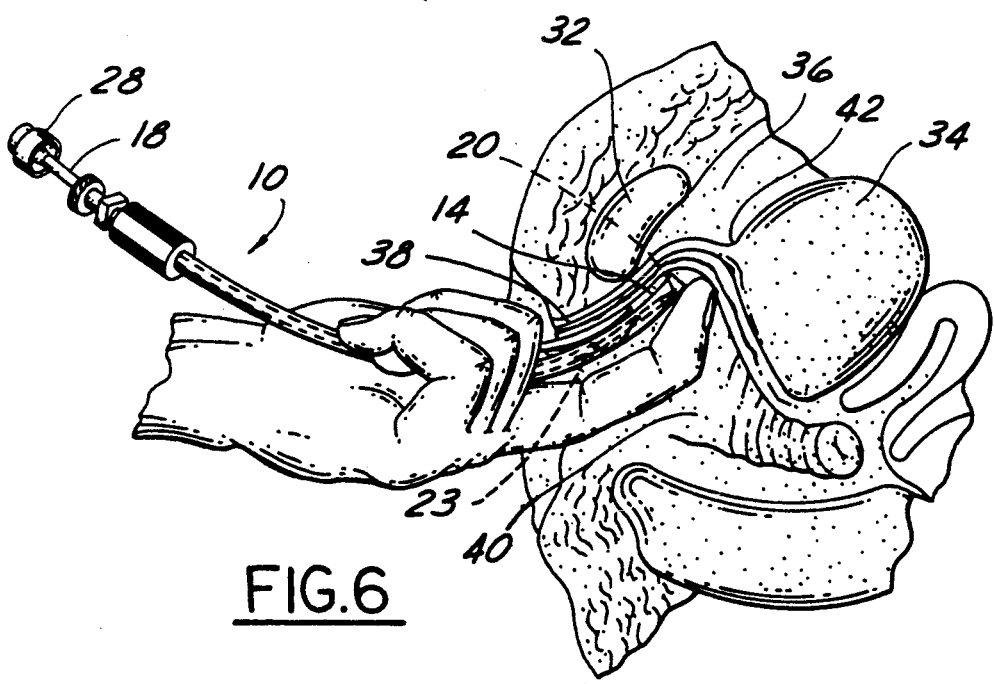
FIG. 6 is a sagittal section through the female reproductive system with the suturing needle assembly poised at the operating site.

Referring now to FIGS. 5, 6 and 7, the method of the present invention can be understood. The procedure begins with an abdominal incision above the pubic bone 32. The surgeon digitally dissects the bladder 34 away from the pubic bone 32 thereby exposing the retropubic space 36. The retropubic space 36 contains the urethra 38 and supporting structures such as the Cooper's ligament 44, the pubic bone 32, and the lateral pelvic sidewall 46 to which surgical sutures will be tied.

The sheath 14 is extended over the needle tip 20 in preparation for its excursion through the vagina 40. The surgeon grasps the suturing needle assembly 10 in his palm, guiding the end of the sheath 14 toward the superior wall of the vagina 40 lying directly beneath the bladder neck 42. When the operating site is reached, the surgeon pushes on the knob 28 located at the end of the flexible portion 18 and propels the needle tip 20 through the superior wall of the vagina 40, under the bladder neck 42, and into the retropubic space 36. Here, the surgeon unhooks one end of the surgical thread 23, holding the thread 23 in the retropubic space 36 as the needle tip 20 is then withdrawn by gently, but firmly applying an outward force on the knob 28. When the tip 20 has been withdrawn to its original location at the superior wall of the vagina, the suturing needle assembly 10 is moved laterally about 2 to 3 cm. and the needle tip 20 is again thrust into the retropubic space 36. The surgeon then removes the other end of the surgical thread 23. The two ends of the surgical thread can then be attached to the Cooper's ligament 44, the pubic bone 32 or the lateral pelvic sidewall 46, thereby effecting an elevation of the bladder neck 42.

To complete the procedure, the suturing needle assembly 10 is withdrawn and supplied with a new surgical thread 23 and the procedure is repeated upon the contralateral side of the superior wall of the vagina with respect to the bladder neck 42.

In light of the foregoing description, it will be apparent that there has been disclosed a suturing needle assembly and a method for its use which allows for an effective treatment for the problem of bladder neck prolapse. The disclosed suturing needle assembly has the characteristics of length and flexibility for accessing internal body tissues, needle sheathing for protection of patient and doctor, and a T-shaped eyelet for simplicity in suture engaging and disengaging.

While the invention has been described in conjunction with a specific embodiment thereof, it is evident that many alternatives, modifications, and variations will be apparent to those skilled in the art in light of the foregoing description. Accordingly, it is intended to embrace all such alternatives, modifications, and variations as fall within the spirit and scope of the following claims.

I claim:

1. A suturing needle assembly for access to an internal body tissue which is accessible by a curved or elongated pathway, the needle assembly comprising:
    an elongated needle having a flexible portion and rigid portion connected thereto, said rigid portion having a tip for piercing the body tissue and defining a means disposed therewithin for removably attaching surgical thread and for securely retaining the surgical thread as the rigid portion is propelled into and is withdrawn from the body tissue; and
    a flexible sheath which is selectively positionable over said cup, said sheath being adapted to bend in cooperation with said needle in response to pressure exerted by a surgeon or by constraints imposed by the cured or elongated pathway.

2. The suturing needle assembly of claim 1 wherein said means for removably attaching the surgical thread comprises an axial eyelet having a transverse aperture.

3. The suturing needle assembly of claim 2 wherein said transverse aperture extends from said axial eyelet to the needle surface so that the surgical thread can be readily engaged thereby and disengaged therefrom.

4. The suturing needle assembly of claim 1 wherein said sheath and said flexible portion are of approximately equal length.

5. The suturing needle assembly of claim 1 wherein said sheath is selectively engagable by said needle so there is no relative axial motion therebetween,.

6. The suturing needle assembly of claim 1 further comprising a cover for shielding said needle and said sheath.

7. The suturing needle assembly of claim 6 wherein said cover slidingly receives said needle and said sheath.

8. A method for performing a surgical procedure involving bladderneck elevation using a suturing needle assembly having a needle and a sheath which is selectively positionable over the needle, the method comprising the steps of:
    making an abdominal incision proximal to pubic bone;
    dissecting the bladder from the pubic bone, thereby exposing a retropubic space;
    elevating a superior wall f a vagina on each lateral side of the bladder neck;
    introducing on each side of the bladder neck a surgical thread using the suturing needle assembly of claim 1 from below the superior wall of the vagina into the retropubic space; and
    binding with said surgical thread the elevated superior wall of the vagina with tissues in the retropubic space, thereby producing an elevation of the bladder neck which aids in the control of bladder discharge.

9. The method of claim 8 wherein said elevating step is performed by the surgeon's finger as the surgeon guides the suturing needle assembly towards the operating site.

10. The method of claim 8 wherein said introducing step further comprises the steps of:
    attaching said surgical thread within an eyelet of the needle;
    extending the sheath over a tip of the needle;
    guiding an end of said sheath towards the operating site through the vagina with the surgeon's finger;
    thrusting said tip through the superior wall of the vagina and into the retropubic space;
    removing a portion of said surgical thread, said portion being held by the surgeon in the retropubic space;
    withdrawing said tip into the vagina;
    moving said tip laterally;
    reintroducing said tip into the retropubic space;
    removing the other end of said surgical thread by engaging said other end by the eyelet of the needle;
    withdrawing the tip back into the vagina; and
    removing the suturing needle assembly from the vagina;

11. The method of claim 8 wherein said binding step comprises binding the superior wall of the vagina to a Cooper's ligament.

12. The method of claim 8 wherein said binding step comprises binding the superior wall of the vagina to the public bone.

13. The method of claim 8 wherein said binding step comprises binding the superior wall of the vagina to a lateral pelvic sidewall.

14. A method for performing a surgical procedure involving bladder neck elevation using a suturing needle assembly having a needle and a sheath which is selectively positionable over the needle, the method comprising the steps of:
    making an abdominal incision proximal to public bone;
    dissecting the bladder from the pubic bone, thereby exposing a retrobpuic space;
    elevating a superior wall of a vagina on each lateral side of the bladder neck;
    introducing on each side of the bladder neck a surgical thread from below the superior wall of the vagina into the retropubic space;
    binding with said surgical thread the elevated superior wall of the vagina with tissues in the retorpbulic space, thereby producing an elevation of the bladder neck which aids in the control of bladder discharge;

attaching said surgical thread within one eyelet of the needle;

extending the sheath over a tip of the needle;

guiding an end of said sheath towards the operating site through the vagina wall surgeon's finger;

thrusting said tip through the superior wall of the vagina and into the retropubic space;

removing a portion of said surgical thread, said portion being held by the surgeon in the retrobpuic space;

withdrawing said tip into the vagina;

moving said tip laterally;

reintroducing said tip into the retropubic space;

removing the other end of said surgical thread;

withdrawing the tip back into the vagina; and removing the suturing needle assembly from the vagina.

* * * * *